(12) United States Patent
Nyholm

(10) Patent No.: US 8,712,010 B2
(45) Date of Patent: Apr. 29, 2014

(54) DIGITAL X-RAY DETECTOR ARRANGEMENT AND DIGITAL X-RAY IMAGING METHOD

(75) Inventor: Kustaa Nyholm, Siuntio (FI)

(73) Assignee: Planmeca Oy, Helsinki (FI)

( * ) Notice: Subject to any disclaimer, the term of this patent is extended or adjusted under 35 U.S.C. 154(b) by 370 days.

(21) Appl. No.: 13/377,033

(22) PCT Filed: Jun. 8, 2010

(86) PCT No.: PCT/FI2010/050470
§ 371 (c)(1),
(2), (4) Date: Dec. 8, 2011

(87) PCT Pub. No.: WO2010/142848
PCT Pub. Date: Dec. 16, 2010

(65) Prior Publication Data
US 2012/0087472 A1    Apr. 12, 2012

(30) Foreign Application Priority Data
Jun. 9, 2009    (FI) .................................. 20090237

(51) Int. Cl.
*G01N 23/04* (2006.01)
(52) U.S. Cl.
CPC ..................................... *G01N 23/04* (2013.01)
USPC ........................................................... 378/62
(58) Field of Classification Search
CPC .............................. A61B 6/0306; G01N 23/04
USPC ..................... 378/19, 98.8, 62, 114
See application file for complete search history.

(56) References Cited

U.S. PATENT DOCUMENTS

| | | | |
|---|---|---|---|
| 6,847,040 B2 | 1/2005 | Strömmer | |
| 2003/0173522 A1 | 9/2003 | Spartiotis | |
| 2004/0017224 A1* | 1/2004 | Tumer et al. | 327/51 |
| 2005/0098735 A1 | 5/2005 | Heismann | |
| 2005/0139757 A1 | 6/2005 | Iwanczyk | |
| 2008/0033673 A1 | 2/2008 | Anton et al. | |
| 2008/0191139 A1* | 8/2008 | Coello et al. | 250/370.09 |

FOREIGN PATENT DOCUMENTS

| | | |
|---|---|---|
| DE | 102006029 184 A1 | 12/2007 |
| WO | WO 98/16853 | 4/1998 |
| WO | WO 03/044565 | 5/2003 |
| WO | WO 2008108734 A1 | 9/2008 |
| WO | WO 2008146230 A2 | 12/2008 |

\* cited by examiner

*Primary Examiner* — Irakli Kiknadze
(74) *Attorney, Agent, or Firm* — Fay Sharpe LLP (57) ABSTRACT

The invention relates to digital imaging implemented using X-radiation and to a detector arrangement designed to be used in such imaging, the operation of said arrangement being based on counters counting signal pulses. In the invention, the detector arrangement comprises switch arrangements which are always connectable to at least two counters and which allow at least one of the counters to be always disconnected from a pixel. It is thus always possible to read out the information from at least one counter while another counter is simultaneously being used for counting signal pulses. The invention provides the advantage that the integration of image information need not be interrupted when information is to be read out from the detector during exposure as a change of the integrating counter can be effected during exposure without losing any image information.

17 Claims, 4 Drawing Sheets

DIGITAL X-RAY DETECTOR ARRANGEMENT AND DIGITAL X-RAY IMAGING METHOD

FIELD OF THE INVENTION

The present invention relates to digital imaging implemented using X-radiation and to a digital detector arrangement for use in such imaging, the operation of said arrangement being based on counters counting signal pulses.

BACKGROUND OF THE INVENTION

X-ray imaging methods can be divided into different sub-types on the basis of many different criteria. For example, full-field imaging generally refers to an imaging method wherein an object is irradiated by a single stationary exposure using an X-ray beam of a size equal to the size of the object and the image information is correspondingly detected by means of an image information receiver of a size equal to or in practice somewhat larger than the object to be imaged. In this context, digital imaging therefore has to be implemented using a detector of the size corresponding to what would be used in case of traditional film imaging. However, detectors having a large image forming surface are expensive, and consequently, depending on the imaging application, it is sometimes more justifiable to use a narrow detector and e.g. an imaging method wherein the object to be imaged is scanned with a narrow radiation beam while the detector is moved on the other side of the object in synchronism with the scanning movement of the radiation beam.

A generally known practice in X-ray imaging is to use radiation-sensitive semiconductor detector surfaces whose basic structure consists of tiny image elements, i.e. pixels, wherein the radiation absorbed in the area of the pixels is first converted to a wavelength of visible light and further into electric signals. Today there are also detectors based on direct detection of X-radiation, wherein X-ray quanta, on being absorbed into the quanta-absorbing medium of the detector, are converted directly into electron-hole pairs, i.e. into charges detectable by electric means. Such media include e.g. biased (photoelectric) Ge, Si, Se, GaAs, HgI, CdTe, CdZnTe or PbI semiconductor materials. Detector elements of this type can be divided into pixels e.g. by using an electric field arranged over them in an appropriate manner such that each one of the electron-hole pairs produced can be collected, avoiding lateral migration, in the area of its respective pixel. Using this kind of technology, it is possible to achieve very high quantum efficiency (dqe), yet without compromising on resolution.

In connection with digital imaging it is not at all rare that a detector technology which is suited for use in a given imaging application or in given imaging applications is poorly or not at all applicable for some other type of imaging. For example, a detector technology designed for taking full-field/radiography images is not necessarily applicable for use in tomography imaging, where the aim is to obtain an image of a layer of an object, and vice versa. There are also differences between tomography techniques due to which a detector technology applicable for use in one technique is not necessarily applicable for use in another technique. A fundamental difference between imaging methods relates to the read-out of information from the detector: in some cases it is required that read-out of image information from the detector should be possible during imaging, whereas in other cases the information is only read out after exposure.

In so-called Frame Transfer (FT) technology, the image information of the entire pixel matrix is repeatedly transferred during exposure to a "shelter" for actual information read-out, i.e. away from the area where image information is received. An FT detector may be based on e.g. so-called CCD or CMOS detector technology, and it can be constructed in several different ways. A typical solution is to divide a CCD element into two sections in such a way that a first section is used for detection of image information while the other section is fitted in a place protected from radiation. In this case, information is transferred in a periodic manner during exposure from the first detector section to the other for read-out, while integration of information still goes on in the detector section unprotected from radiation. However, this gives rise to the problem typically associated with FT imaging that the information integrated in the pixels during transfer of image information causes undesirable blurring of the (partial) image being transferred to storage. Moreover, many detector solutions designed for FT imaging are ill-suited or completely unsuited for use in more than one type of imaging.

In principle, it might be possible to avoid the above-discussed undesirable blurring of the image by always momentarily interrupting either the irradiation of the object or the integration of the information for the duration of transfer of image information. However, in many applications, always interrupting irradiation for the duration of information transfer is an unrealistic alternative difficult to implement. On the other hand, interruption of integration again would lead to a loss of that portion of the information descriptive of the object being imaged which is produced by irradiation of the object during integration. This would naturally be a quite unsatisfactory solution e.g. in conjunction with x-ray imaging of humans, wherein all unnecessary irradiation of the object to be imaged is undesirable or even forbidden by orders of the authorities. On the other hand, depending on the detector technology being used, interruption of integration for the duration of information readout would not necessarily be even technically possible. Further, if the imaging method additionally involves some specific mutual relative movement between the object and the imaging means, then the situation is even more problematic as in that case it would in principle be necessary to stop such movement as well for the duration of interruption of irradiation or integration.

Patent specification U.S. Pat. No. 6,847,040 discloses a detector solution which, among other things, makes possible both full-field imaging and scanning imaging implemented by the TDI technique using a technology whereby the image information produced by X-ray quanta having penetrated the object to be imaged is detected by counting the number of X-ray quanta absorbed. In the detector described in this specification, pixel values are shifted by loading the counters from the counters of the preceding column, and the information is read out from the last column via a shift register arranged at the edge of the detector. The detector technology described in the specification is especially designed to enable imaging by the so-called TDI technique, in which it is required that pixel values can be shifted and integration of image information carried on pixel column by pixel column as a function of the speed of propagation of the radiation beam in the object. However, the technique in question is not optimal e.g. for a type of imaging in which the information integrated in the counters at a given instant of time should be recovered in real time during exposure, because during the column-by-column shifting of the information there would also be integrated in the pixel values other information besides that descriptive of those points of the object intended to become imaged.

In detectors employing counters, the read-out of image information can be implemented using read-out electronics arranged on the surface of an amorphous silicon substrate. The detector can also be arranged to consist of smaller modules and the read-out electronics can be implemented using CMOS (Complementary Metal-Oxide Semiconductor) technology. For example, in a detector of the type presented in WO specification 98/16853, it is possible to arrange for each pixel to be selected at a time and for the information to be read out via a signal bus extending to the edge of the detector. The arrangement makes it possible, among other things, to read out the information from individual pixels in real time during exposure. However, considering a pixel matrix consisting of a plurality of pixels as a whole, the larger the matrix, the larger is always the time difference between the information of the pixel of the matrix read out first and that of the pixel read out last. Such a non-simultaneity may cause distortions in the image being formed that in practice prevent this detector technology in question from being used for real-time imaging, i.e. for imaging where information is read out from the detector without interrupting the exposure.

When prior-art technologies as described above are used, and especially in the case of a larger pixel matrix, reading out the information from the detector inevitably always takes that much time that distortions may be produced in the image being formed. The use of detector technology employing counters does not in itself eliminate the above-described problems relating to real-time imaging.

BRIEF DESCRIPTION OF THE INVENTION

The object of the present invention is to improve the state of the art associated with detector technology employing counters and to achieve a detector arrangement and method wherein it is possible to exploit the possibilities provided by the technology based on the use of counters and at the same time to achieve a solution that, in particular, enables real-time imaging of the above-described nature. On the other hand, various embodiments of the invention enable diversified use of the same detector structure e.g. for full-field, scanning and tomography imaging, as well as read-out of information from the detector e.g. according to both the TDI and the FT principle. The aim of the invention is to enable image information to be read out from the detector during imaging in such a way that irradiation of the object and integration of the information can be continued without interruption and without being disturbed by read-out of information.

Thanks to the invention and its different embodiments, neither irradiation nor integration of image information need be interrupted due to information read-out. On the other hand, it is possible to arrange for information to be read out from the detector according to the prerequisites of the imaging application used in each case either during imaging or only after it. The invention and its preferred embodiments enable diversified use of the same detector technology or, depending on the application, even the same detector, for example the use of the same detector in a given imaging application but with different imaging techniques. The price of imaging detectors is essentially dependent on the development costs of the detector, the proportion of which will naturally be lower if the same microchip can be used in more than one application.

The features characteristic of the invention are presented in the attached independent claims, and preferred embodiments of the invention are presented in the attached dependent claims. The invention is based on the insight that, when a prior art detector utilizing counter technology is provided with means that allow image information detected by pixels and delivered in pulse form to counters to be alternatively passed to at least two counters in a counter arrangement comprising at least two counters, then it is possible to arrange for at least one counter to be used for integration of image information while the information integrated by another counter is simultaneously being read out. When the detector is provided with switch arrangements always connectable to at least two counters and always allowing at least one of the counters to be disconnected from a pixel, it is always possible to read out information from at least one counter while another counter is simultaneously being used for counting signal pulses. There are naturally several different ways of implementing such a switch arrangement. For example, it is possible to provide a separate switch for each counter comprised in the arrangement, or it is possible to use a switch arrangement that allows selection of the counter or counters which are to count pulses in each situation. The invention provides the advantage that integration of image information need not be interrupted on account of the integrating counter being changed to be another one by changing a switch position or switch positions, thus the change can be performed during exposure without losing any image information.

As compared to prior-art solutions, the counter/switch arrangement unit according to the present invention enables considerably more diversified use of the detector with a small enough addition of electronics and provides a solution particularly well suited for expressly real-time imaging. In some of its embodiments, the invention makes it possible to use the same digital camera in different imaging applications and to obtain in the same imaging application diversified information about the object being imaged. For example, in dental panoramic X-ray imaging, whereby a tomography image of the skull is taken using a narrow scanning radiation beam to produce a planar image of a dental arc, it becomes possible to use the same detector according to the invention for both TDI and Frame Transfer (FT) type imaging, and, with suitable arrangements, even to take such images formed on different principles by a single imaging scan. If only FT imaging is considered, the invention provides the advantage of enabling practically complete avoidance of the hard-to-control undesirable image blurring that in the prior art solutions typically always occurs to some degree when an arrangement is used where image information is transferred on the detector during exposure without interrupting integration for the duration of the transfer.

BRIEF DESCRIPTION OF THE FIGURES

In the following, the invention will be described in detail using some of its preferred embodiments as examples. In the attached drawings

DETAILED DESCRIPTION OF THE INVENTION

Figure 1:
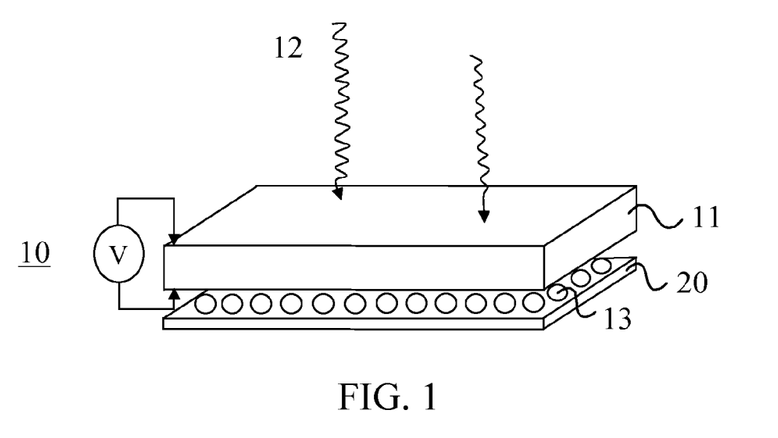
FIG. 1 presents a construction of one detector based on direct detection of X-radiation.

FIG. 1 shows the basic structure of a detector 10 based on direct detection of X-radiation, in which the element 11 used to absorb X-radiation 12 is a material layer having a size of X\*Y and converting the radiation directly into an electric signal, which material layer is placed in an electric field V. The material layer in question may consist of e.g. a relatively thin semiconductor material structure (Ge, Si, Se, GaAs, HgI, CdTe, CdZnTe, PbI), in which that surface which in FIG. 1 is not visible, opposite to the surface facing towards the X-radiation 12, is provided with pixel electrodes arranged so as to cover the detector in a desired manner. The electric field V collimates the signal generated in the detector for each respective pixel and the signal can be detected e.g. by means of indium ball coupling 13 connecting to each pixel electrode, and a substrate comprising read out electronics and having a surface area substantially equal to that of the semiconductor-based absorption element 11. The read-out electronics 20 may be implemented using e.g. CMOS technology.

Figure 2:
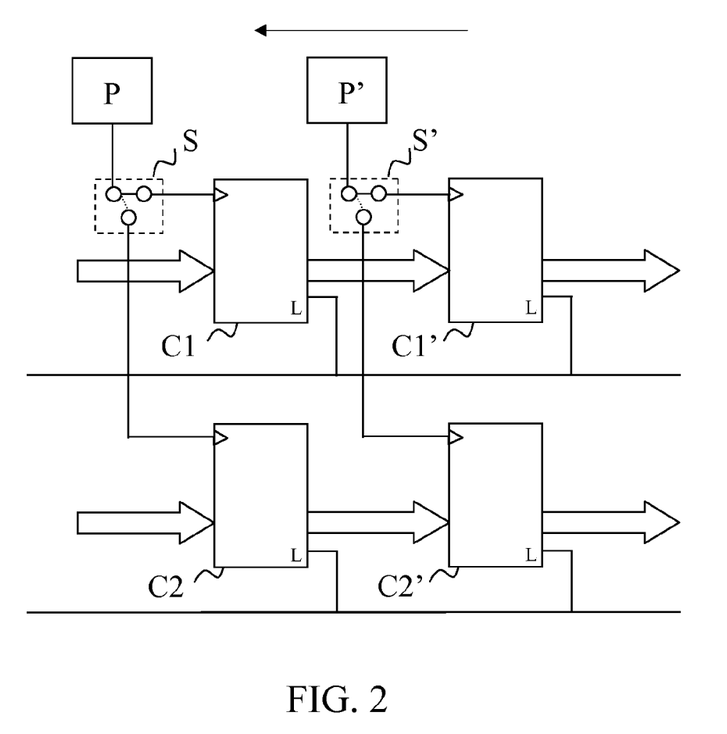
FIG. 2 presents a counter/switch arrangement according to one preferred embodiment of the invention, comprised in the detector arrangement.

FIG. 2 presents a switch-counter arrangement comprised in one preferred embodiment of the invention. In the embodiment according to FIG. 2, pixels P, P' are arranged to be optionally connected to the inputs of counters C1, C2; C1', C2' by switches S, S'. The positions of the switches S, S' can be controlled by control signals according to the requirements of the imaging process in question. Exposing the object being imaged needs not be interrupted when the pulses which have been integrated e.g. in the first counters C1, C1' are being read out, as one may shift to counting pulses coming from the pixels P, P' by the second counters C2, C2' for the duration of read-out of the first counters C1, C1'. The counters C1, C2; C1', C2' may be e.g. 12-16-bit digital counters, counting voltage or current pulses fed to them. The counters can be provided with a circuit that prevents counting after the counter has reached its maximum count. Consequently, overexposure will not lead to an overflow, but the only "error" in the image caused by the overexposure is that the pixel signal one measures is at its maximum value. Naturally, the invention can also be implemented using other types of counters.

In FIG. 2, the large arrows shown in connection with the counters C1, C1'; C2, C2' visualize the way in which counter pairs C1, C2; C1', C2' in this detector arrangement according to the invention can be connected to each other in the direction of the pixel rows (or, in the case of scanning imaging, in the direction of the imaging scan movement used in the imaging process; thin arrow in FIG. 2) so that counters C1', C2' can be loaded from the corresponding counters C1, C2 in the preceding pixel column. In the solution according to FIG. 2, this loading of the counters C1, C1'; C2, C2' is controlled by clock signals L. With this arrangement, a pixel row C1, C' can be read out e.g. via the last counter in the row while the counters C2, C2' in the second counter row are simultaneously integrating the pulses being received from the pixels P, P'.

The arrangement represented by FIG. 2 can also be used as a detector enabling traditional TDI imaging simply by keeping the switch S, S' associated with each pixel P, P' connected to one and the same counter for the duration of the whole exposure (in other words, by keeping the switches S, S' connected either to counters C1, C1' or to counters C2, C2').

Figure 3A:
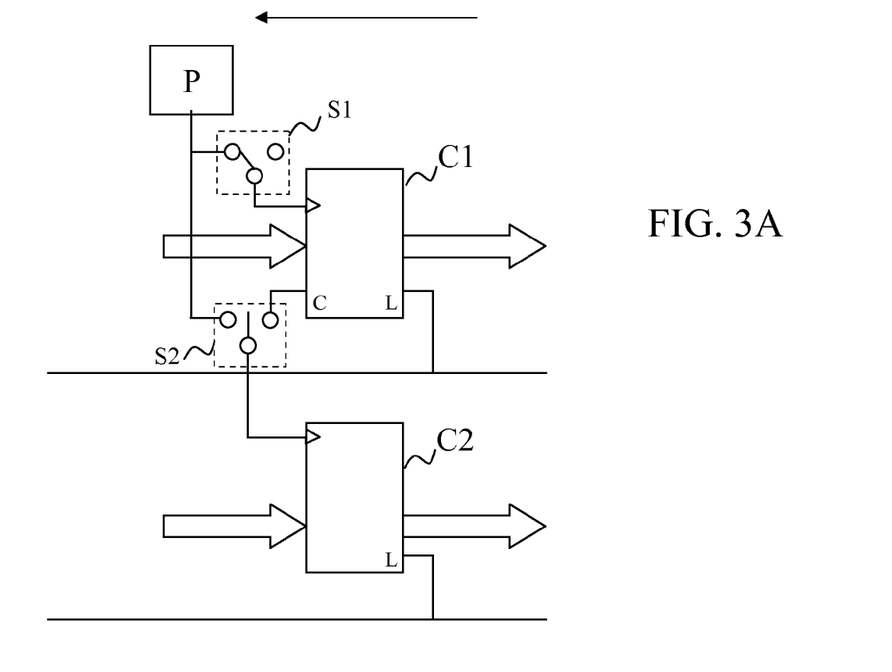
FIGS. 3A-3D present counter/switch arrangements of a detector according to a second and a third preferred embodiment of the invention in different operational situations.
Figure 3B:
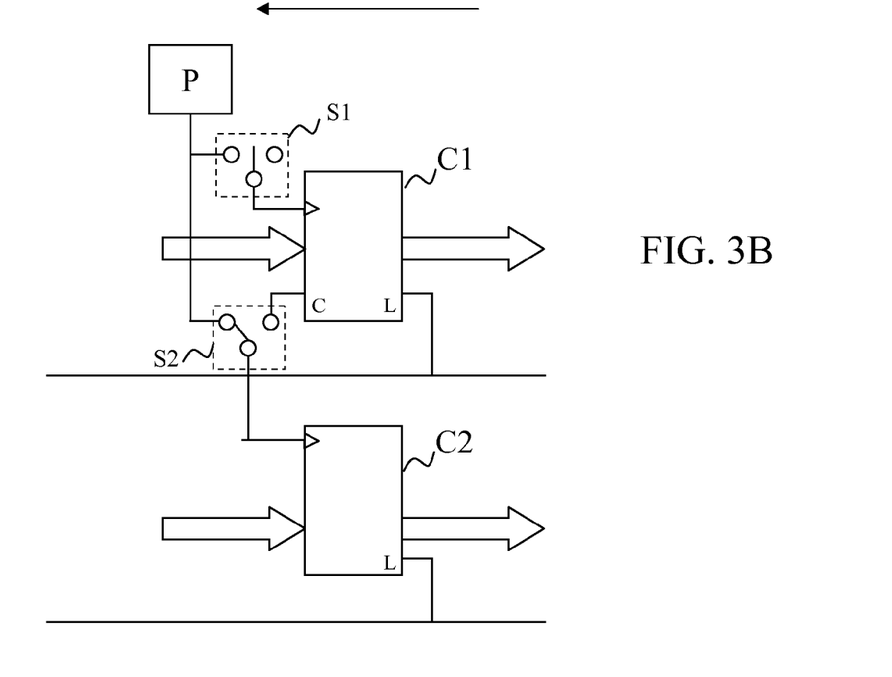
Figure 3C:
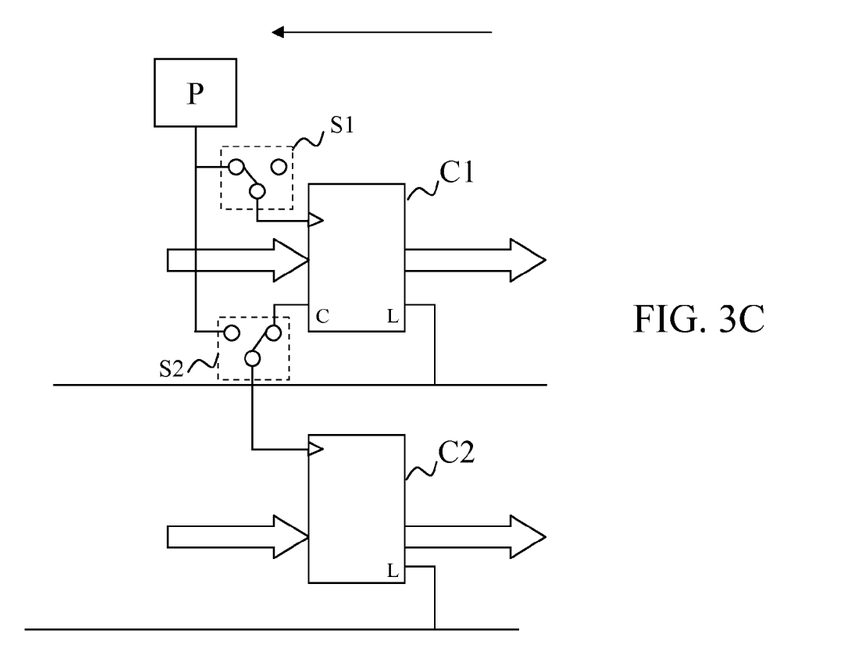

FIGS. 3A-3C present an arrangement according to another preferred embodiment of the invention, wherein the switch arrangement comprises two switches S1, S2 instead of a single one. In the situation visualized in FIG. 3A, the pixel P is connected by switch S1 to the input of counter C1, whereas no connection is made to the input of counter C2. In the situation visualized in FIG. 3B again, no connection is made to the input of counter C1 while the pixel P is connected by switch S2 to the input of counter C2. Thus, by alternating the positions of the switches S1, S2 according to FIGS. 3A and 3B, this embodiment of the invention can be used on the same principle as the solution presented in FIG. 2 e.g. for real-time imaging with no need to interrupt irradiation for the duration of read-out of information. In this case, the switches S1, S2 are thus controlled in such manner that, when the switches S1, S2 are in the position shown in FIG. 3A, i.e. when switch S1 connected to the input of counter C1 passes the signal coming from the pixel P to the input of this counter while the input of counter C2 is not connected to receive any signal, the arrangement is in a mode where the first counter C1 is integrating the information received from the pixel P. When the switches are turned to the position shown in FIG. 3B, i.e. by cutting off the connection between the pixel P and the input of the first counter C1 and connecting the input of the second counter C2 to the pixel P, integration can be continued in the second counter C2'—and thus without a need to interrupt integration for the duration of reading out the first counter C1. Thus, by alternating the switch positions in the above-described manner between different positions, it is possible in this embodiment of the invention to implement real-time imaging in such a way that, always when one counter (or e.g. a complete counter row) is being read out, another counter (row) is counting. Using the arrangement presented in FIGS. 3A-3B, it is possible to implement the same functionalities as those described above in conjunction with FIG. 2, such as the loading of counters from corresponding counters in an adjacent pixel column.

FIGS. 3A and 3B thus present an embodiment wherein a pixel P is connectable by separate switches S1, S2 to the input of either one of the counters comprised in the counter pair in question. In this embodiment, the input of the second counter C2 is additionally arranged to be connectable by switch S2 to the first counter C1 as well, as shown in FIG. 3C. When the switches S1, S2 are in the positions shown in FIG. 3C, in other words, when the input of the first counter C1 is connected to the pixel P and the input of the second counter C2 is connected to the first counter C1, the counter pair C1, C2 has been connected to function as a single counter. By connecting the counters C1, C2 in series in this manner, the available counting capacity is increased, i.e. it is possible to count larger numbers, because the second counter C2 can be used e.g. to count pulses generated as a consequence of the first counter C1 reaching its maximum count. The arrangement represented by FIG. 3C functions in such a way that, after counter C1 has reached its maximum count, the next pulse entering counter C1 generates a carry-out pulse C which is passed from counter C1 via switch S2 to counter C2, and this pulse is counted by counter C2 while counter C1 resets to its initial value. As compared to the embodiment presented in FIG. 2, in which it is not possible to connect the counters C1, C2 in series but instead at each instant of time only one of the counters can be used for integration, the arrangement according to FIG. 3C provides the possibility to utilize the full counting capacity of the detector arrangement e.g. when it is used for TDI imaging as described in connection with FIG. 2. In a corresponding manner, it is also possible to arrange more than two counters C1, C2 connected in series, in which case consecutive counters area arranged to function in a manner corresponding to that described above. A carry-out pulse to the next counter can be arranged to be produced, besides in response to the preceding counter reaching its maximum count, also in response to the preceding counter reaching a preset value.

Figure 3D:
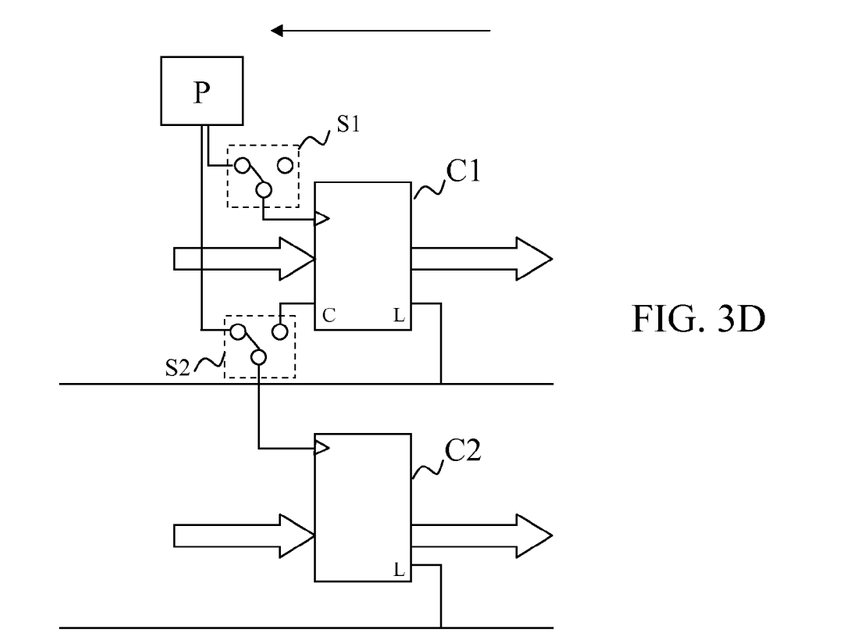

FIG. 3D presents a third embodiment of the invention, which is based on the switch-counter arrangement presented in FIGS. 3A-3C. The arrangement in this embodiment comprises two parallel outputs from a pixel P for directing e.g. pulses having different energy levels via two separate switches S1, S2 to be counted by separate counters C1, C2. In this case, the electronics of the detector arrangement may at the pixel level comprise signal amplifiers and comparators, for example, which are not shown in the figure and which, e.g. according to reference levels externally adjustable as desired, either do or do not detect a quantum absorbed into the area of the pixel P. A pulse can be arranged to be counted when its energy exceeds the reference level, but in some applications it is also possible to count pulses with an energy level below a desired threshold level. Various embodiments of the invention permit, among other things, the use of several different threshold energy levels so that separate counters C1, C2 are only fed with e.g. pulses below certain different maximum energy levels, or pulses within a given energy level range. To maintain simplicity of the drawing, such portion of the switch arrangement is not shown in FIG. 3D whereby pulses can be directed according to the invention from both outputs of the pixel P presented in FIG. 3D optionally to at least two different counters. Such arrangements can naturally be implemented in several different ways.

According to the invention, it is also possible to implement arrangements in which more than two counters are used and/or in which pulses received from pixels can be passed simultaneously even to more than one counter. The criterion on which pulses are passed to more than one counter may also be other than the energy level of the X-ray quanta. Integration by different counters can also be effected in such time cycles that it will take place completely or partly simultaneously, and while at least one counter is integrating, even more than one non-integrating counter can be read out. For example, scanning imaging can be implemented in such a way that at least two of the counters comprised in a switch-counter arrangement unit according to the invention are controlled by different clock signals to produce e.g. a radiograph (a transillumination image) and a tomogram (a layer image), or to produce different tomograms with the same imaging scan. Further, pulses can be passed to different counters e.g. in synchronism according to some periodically varying imaging parameter value of the radiation source.

It is further conceivable to use e.g. the arrangement according to FIG. 3D in such manner that e.g. counter C1 is used conventionally for integration of image information pulses whereas counter C2 and the associated switch S2 are controlled in such a way that the signal is integrated for only a short time, whereupon it is read out to be utilized in an automatic exposure function controlling the exposure. The signal for the automatic exposure function can conceivably also be read e.g. from the arrangement according to FIGS. 3A-3C in such a way that pulses are integrated for a short time e.g. in counter C2, whereupon a changeover is performed to make counter C1 the integrating counter and the information integrated in counter C2 is read out for use in the automatic exposure function. Further, by using suitable arrangements obvious to a skilled man thus not to be described here in detail, the information used in the automatic exposure can be arranged to be later incorporated in the image information itself.

In the foregoing, the description relating to FIGS. 2 and 3A-3D presents some embodiments of the invention in which the arrangement permits the counters to be loaded from the preceding corresponding counters in the detector matrix. The solution in question provides a simple method for reading out the results from the counters, but of course it is also possible to arrange for the information to be read out e.g. directly from each counter.

Figure 4A:
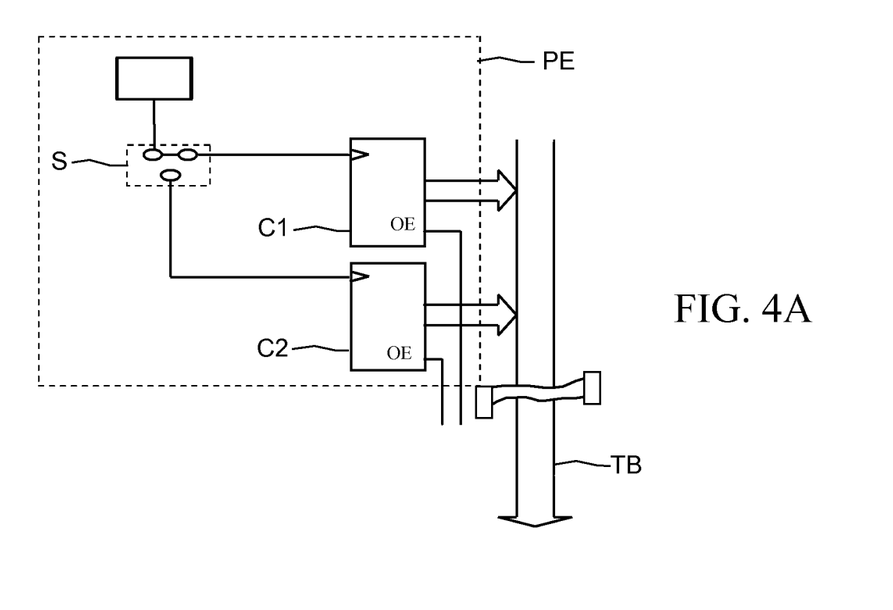
FIGS. 4A and 4B present arrangements for the reading out of image information from the detector.

FIG. 4A represents an embodiment which may be used for reading out image information, wherein the switch arrangement S corresponds to the solution presented in FIG. 2. In FIG. 4A, the reading out of the (at least) two counters C1, C2 comprised in the pixel element PE into the transfer bus TB is controlled by control signals OE (output enable). Assuming that the pixel element PE in FIG. 4A is one of the pixel elements in the outermost pixel column of the pixel matrix of the detector and that each counter C1, C2 in the pixel elements of the matrix in question is arranged as described above to be loaded from the corresponding counter in the preceding column, the arrangement according to FIG. 4A could be used e.g. in TDI imaging, but also even in FT imaging.

Figure 4B:
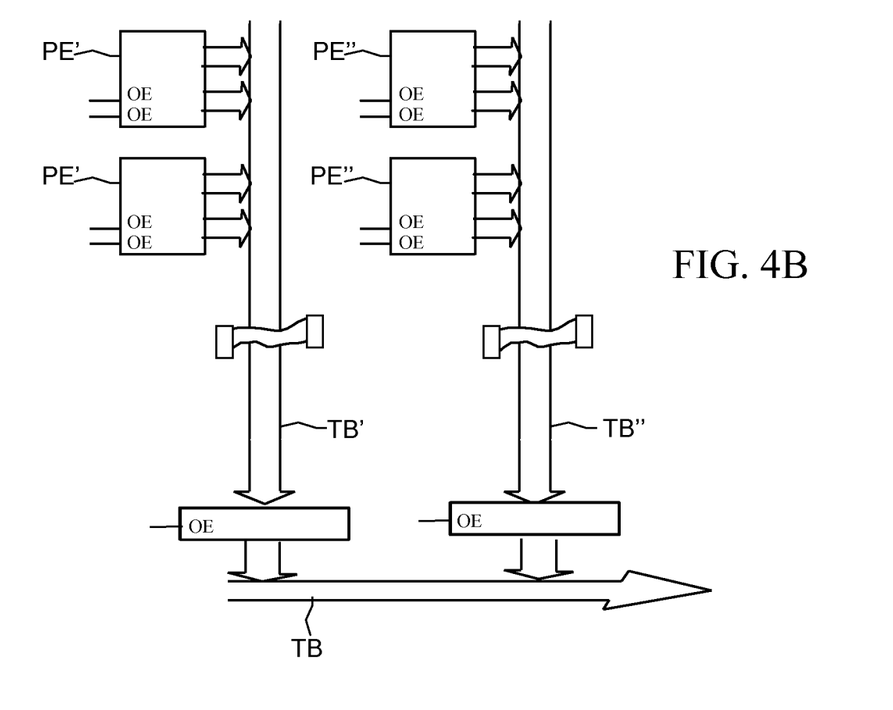

FIG. 4B can be conceived of as representing transfer buses TB', TB" covering the columns of a matrix comprising pixel elements PE', PE". Via each transfer bus, information can be read out separately from each column as controlled by control signals OE. The arrangement allows the information of e.g. certain counters in each pixel column to be read out column by column, which solution is advantageously applicable for use e.g. in real-time Frame-Transfer type imaging and therefore e.g. in digital dental panoramic imaging. On the other hand, using the control signal arrangement presented in FIG. 4B, it is also possible to read out the information of any individual pixel element or elements.

It is obvious to a man skilled in the art that, with the development of technology, the fundamental concept of the invention can be implemented in many different ways. Thus, the invention and its embodiments are not limited to the above-described examples but can be varied within the scope defined by the claims below. For example, the implementation of the invention does not preclude the possibility of arranging for the signal detected by a pixel to be directed to a switch-counter arrangement unit according to the present invention in ways other than those described above—such as by using between the counters and the pixels connectable to them some other components besides the switch arrangements according to the invention. For example, U.S. Pat. No. 7,145,985 discloses a solution where pulses can be passed to an individual counter from more than one pixel by means of a switch arrangement according to the invention in question. Thus it is possible to apply the present invention even in that context by arranging switch-counter arrangement units according to the present invention in conjunction with pixel-switch arrangement units according to this US patent specification—that is, in practice by replacing the counters in that pixel-switch arrangement with switch-counter arrangement units according to the present invention. In this way, each signal coming from a pixel group-switch arrangement unit according to U.S. Pat. No. 7,145,985 can be arranged to be passed by means of a switch-counter arrangement according to the present invention optionally e.g. to one of the two counters comprised in such an arrangement, in which case the switch-counter units of the present invention are not directly connected to mutually adjacent individual pixels but to such mutually adjacent components comprised in the detector arrangement that are functionally connected to pixels.

In the light of the above-described embodiments, the fundamental concept of the present invention can be characterized in more general terms by stating that the essential principle of the invention is to use a digital detector arrangement comprising pixels, which detector arrangement comprises counters for counting image information pulses and is arranged to comprise several units each one of which comprises at least two counters and a switch arrangement comprising one or more switches, said units being arranged to be connected either to mutually adjacent pixels or to mutually adjacent components of the detector arrangement that are functionally connected to one or more pixels, and in which aforesaid unit the switch arrangement is adapted to enable a pixel, or said component functionally connected to a pixel or pixels, to be optionally connected to at least two of the aforesaid counters and thus to enable the aforesaid pulses received from the pixels to be directed to at least one counter being selected at the time.

The detector of the invention utilizing counter technology can be used e.g. in both traditional stationary radiography (transillumination imaging) and one performed by the scanning technique, as well as in different tomography imaging procedures. For example, different tomography procedures are feasible by arranging for the frequencies of the counter loading functions performed pixel column by pixel column to be synchronized in a desired manner with the scanning movement of the radiation beam. The counters in the first column of the detector can be arranged to be loaded to zero, thus allowing the detector signal to be easily set to zero. The results from different counter rows can be combined e.g. in connection with signal read-out by techniques known per se. For example, in an arrangement comprising a number of pixel rows and columns, the results from the outermost counters can be arranged to be loadable in parallel into a shift register—in the case of scanning imaging using the TDI method, expressly into a shift register on the trailing edge side of the detector—which then by using a serial transfer transfers the bits out one after the other. It is possible to use the detector both in applications where the image information is read out only after the imaging, and e.g. for scanning imaging by the TDI or FT method in a manner requiring at its minimum only one output signal for the read-out of the entire image data produced by the detector. Even more generally speaking, all the connections presented in FIGS. 2, 3A-3D can be arranged to be used for scanning imaging by the TDI technique as well as e.g. for taking individual full-frame images (FF), in addition to the fact that they naturally also provide a possibility for real-time imaging according to the primary inventive concept of the invention by alternating during irradiation the integrating counter and the counter to be read out. It is also possible to utilize the invention by using other arrangements and methods for reading out the counters than those described above, e.g. in conjunction with a modular detector arrangement. In the figures of the present application, the thick arrow representing the loading of counters may in practice stand for either serial-mode or parallel-mode data transfer. Besides dental X-ray imaging, such as panoramic imaging as mentioned above, the solution of the invention can conceivably also be used e.g. in mammography and various CT (Computed Tomography) imaging procedures.

The invention claimed is:

1. A digital X-ray detector arrangement, which includes a detector including a number of pixels (P), in conjunction with which detector are arranged an X-radiation absorbing element (11), a means for passing on the information detected by the pixels (P) in the form of pulses and counters (C1, C2) for counting the pulses received from the pixels (P), characterized in that there are arranged in the detector several units each one of which comprising at least two counters (C1, C2) and a switch arrangement comprising one or more switches (S, S1, S2), that the aforesaid units are arranged to be connected either to i) mutually adjacent pixels (P) or to ii) mutually adjacent detector components that are functionally connected to one or more pixels (P), and that in the aforesaid units said switch arrangement is adapted to enable a pixel (P), or said component functionally connected to one or more pixels (P), to be optionally connected to at least two of the aforesaid counters (C1, C2) and thus to enable the aforesaid pulses received from the pixels to be directed to the at least one counter (C1, C2) being selected at the time.

2. The detector arrangement according to claim 1, characterized in that it includes a control system, which includes means for controlling the aforesaid switches (S, S1, S2) so that pulses are passed during exposure in a periodic manner to at least two different counters (C1, C2), and/or a means for controlling the switches (S, S1, S2) so that pulses are passed during exposure in a continuous manner to at least two different counters (C1, C2).

3. The detector arrangement according to claim 1, characterized in that it includes a control system including control means for controlling the aforesaid switches (S, S1, S2) and counters (C1, C2) so that, simultaneously when at least one of the counters (C1, C2) is counting the pulses transmitted to the counter (C1) in question via the switch arrangement (S, S1, S2), at least one other counter (C2) is not connected via the switch arrangement (S, S1, S2) to receive pulses and that at least one counter (C2) in question is read out.

4. The detector arrangement according to claim 1, characterized in that it includes a means for detecting pulses having at least two different energy levels and a control means for switching the switches (S, S1, S2) in the aforesaid switch arrangement in such a way that said pulses of at least two energy levels are passed to their respective counters (C1, C2).

5. The detector arrangement according to claim 1, characterized in that the arrangement comprises a means for connecting at least two counters (C1, C2) in series to form from the counters (C1, C2) concerned a counter having a larger counting capacity, in other words, a means (C) for transmitting a pulse to the input of the next counter (C2) in response to the preceding counter (C1) having reached its maximum count or a preset value.

6. The detector arrangement according to claim 1, characterized in that the aforesaid number of pixels (P) are arranged to form rows comprising several mutually adjacent pixels (P), said pixels (P) thus forming a matrix comprising pixel rows and columns, and that the arrangement comprises a means for loading the counters (C1, C2) belonging to such a pixel row from corresponding counters (C1, C2) in the preceding pixel column.

7. The detector arrangement according to claim 1, characterized in that it includes a control system including a means for controlling the aforesaid switch arrangement (S, S1, S2) so as to cause them to direct said pulses to different counters (C1, C2) in a desired periodic manner, said periodicity being synchronized according to a periodically changing parameter value of the radiation source used for the imaging, and/or a means for controlling the aforesaid switch arrangement (S, S1, S2) for collecting a signal for an automatic exposure function used in the imaging.

8. The detector arrangement according to claim 1, characterized in that the aforesaid pixels (P) are arranged to form a number of pixel rows and/or pixel columns, and that the arrangement comprises a means for reading the result from at least some of the counters (C1, C2) into at least one transfer bus (TB), such a transfer bus (TB) being provided in conjunction with all the pixel columns, with several of the pixel columns or only with the outermost pixel column.

9. The detector arrangement according to claim 1, characterized in that it is arranged to form a part of a dental imaging arrangement, comprising means for scanning the object to be imaged with a narrow radiation beam, and that the imaging arrangement comprises means for controlling the detector during the imaging scan according to the principles of the FT (Frame Transfer) imaging method known per se in such a way that, each time when, during scanning, the information of one partial image is to be read out, the passage of pulses to the counter (C1, C2) having integrated the information relating to that partial image in question is cut off and one begins to direct the pulse flow to another one of said at least two counters (C1, C2).

10. A digital X-ray imaging method, wherein the object to be imaged is irradiated by an X-ray beam, image information is integrated in a detector arrangement which comprises a number of pixels (P) and in which radiation quanta are converted into pulses, and pulses are passed into counters (C1, C2) functionally connected to the pixels (P) to count the pulses, characterized in that said pulses are passed into units, each one of which comprising at least two counters (C1, C2) and a switch arrangement (S, S1, S2) comprising one or more switches (S, S1, S2), that the aforesaid units are arranged to be connected either i) to mutually adjacent pixels (P) or ii) to mutually adjacent detector components that are functionally connected to one or more pixels (P), the switch arrangement in the aforesaid units being adapted to enable a pixel (P), or said component functionally connected to one or more pixels (P), to be optionally connected to at least two of the aforesaid counters (C1, C2), and that aforesaid pulses received from the pixels (P) are passed to the at least one counter (C1, C2) being selected at the time.

11. The method according to claim 10, characterized in that the switches (S, S1, S2) and counters (C1, C2) are controlled in such a way that pulses are passed in a periodic manner to at least one of said counters (C1, C2) and, simultaneously when said at least one counter (C1, C2) is counting said pulses, another counter (C1, C2) is being read out, and/or that said switches (S, S1, S2) are controlled in such a way that pulses are passed simultaneously to at least two counters (C1, C2).

12. The method according to claim 10, characterized in that the switches (S, S1, S2) are controlled in such a way that the one or more switch/switches (S, S1, S2) that is/are connected to a counter or counters (C1, C2) at the start of exposure are held in this connection throughout the duration of the exposure.

13. The method according to claim 10, characterized in that said pulses are passed during exposure to a counter combination consisting of at least two counters (C1, C2) in such manner that, each time the preceding counter (C1) has reached its maximum count or a predefined value, it is reset to its initial value and at the same time a pulse, which is to be counted, is delivered to the input of the next counter (C2) via a circuit connecting the counters (C1, C2) in question.

14. The method according to claim 10, characterized in that pulses having at least two different energy levels are detected and said pulses of at least two energy levels are passed to their respective counters (C1, C2).

15. The method according to claim 10, characterized in that the object to be imaged is irradiated in a periodic manner using variable imaging parameters and said switches (S, S1, S2) are controlled in synchronism with the frequency of variation of the values of said imaging parameters, such as to always direct pulses corresponding to each combination of radiation source parameter values to a certain same counter or certain same counters (C1, C2).

16. The method according to, claim 10 characterized in that the imaging is performed using a narrow radiation beam scanning across the object to be imaged and the aforesaid detector arrangement is controlled according to the principles of FT (Frame Transfer) imaging known per se in such a way that, each time when, during scanning, the information of one partial image is to be read out, the passage of pulses to the counter (C1, C2) having integrated the information relating to the partial image in question is switched off and one starts to direct the pulse flow to another one of said at least two counters (C1, C2).

17. The method according to claim 10, characterized in that the imaging is performed using a narrow radiation beam scanning across the object to be imaged and the aforesaid detector arrangement is controlled according to the principles of TDI imaging known per se in such a way that said pulses are passed by means of said switch arrangement to at least one of said counters continuously throughout the duration of the imaging scan.

* * * * *